United States Patent [19]

Sonneborn et al.

[11] Patent Number: 4,508,833
[45] Date of Patent: Apr. 2, 1985

[54] SEPARATION OF INTERLEUKIN-2 FROM PHYTOHEMAGGLUTININ BY DYE MATRIX CHROMATOGRAPHY

[75] Inventors: Hans H. Sonneborn, Heusenstamm; Udo Schwulera, Bad-Vilbel; Hans Schleussner, Frankfurt, all of Fed. Rep. of Germany

[73] Assignee: Biotest-Serum-Institut GmbH, Frankfurt, Fed. Rep. of Germany

[21] Appl. No.: 449,708

[22] Filed: Dec. 14, 1982

[30] Foreign Application Priority Data

Dec. 12, 1981 [DE] Fed. Rep. of Germany ....... 3149360

[51] Int. Cl.$^3$ ............... G01N 31/08; A61K 37/02; B01D 15/08
[52] U.S. Cl. ................... 436/543; 436/807; 210/660; 210/672; 210/927; 260/112 R; 424/88; 514/2
[58] Field of Search ............... 436/548, 543, 807, 501; 260/112 R; 210/198.2, 905, 925, 30-35, 660-663, 670-672, 927; 435/68, 172.2; 424/88, 177

[56] References Cited

U.S. PATENT DOCUMENTS 4,355,017 6/1982 Miles et al. .................... 252/430
4,390,623 6/1983 Fabricus et al. ................. 435/68
4,404,188 9/1983 Donahoe et al. ................. 424/105
4,406,830 9/1983 Fabricius et al. .............. 260/112 R

OTHER PUBLICATIONS

Dye-Ligand Chromatography, Amicon Corporation, Publication 512, Lexington, Mass. (1980), pp. C2–C37.

Primary Examiner—Ben R. Padgett
Assistant Examiner—M. Moskowitz
Attorney, Agent, or Firm—Sprung Horn Kramer & Woods

[57] ABSTRACT

Crude interleukin-2 extract is subjected to group-selective dye-ligand absorption chromatography in one or more stages of purification with a matrix-gel medium consisting of a Blue A ligand or variant thereof or of a Green A ligand in a concentration of approximately 1.5 to 3.0 mg/ml of expanded matrix at a pH of approximately 6.8 to 8.5, a temperature of approximately 4° to 40° C., and a flowthrough rate of approximately 10 to 100 ml/h, employing an eluent. Either PHA-free or extremely pure interleukin-2 is obtained, depending on the overall number of purification stages.

6 Claims, 3 Drawing Figures

SEPARATION OF INTERLEUKIN-2 FROM PHYTOHEMAGGLUTININ BY DYE MATRIX CHROMATOGRAPHY

The invention is a method of purifying human interleukin-2 and/or separating phytohemagglutinin from it.

Interleukin-2, abbreviated IL-2 and previously called T-cell growth factor, abbreviated TCGF, is a lymphokine protein molecule synthesized by lymphocytes stimulated with antigen or mitogen. It occupies a position of central importance in cellular immunodefense. To it is attributed the clonal multiplication of lymphocytes previously activated by antigen or mitogen.

Figure 1:
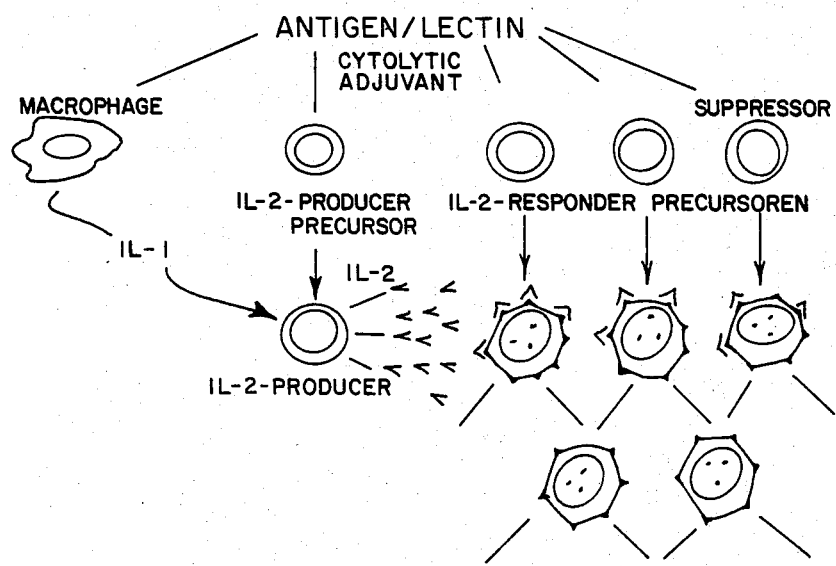

FIG. 1 shows a model of T-cell activation in accordance with which interleukin-2 (TCGF) is formed from TGCF producers (a T-cell sub-population). The factor then affects what are called TCGF responders that have formed TCGF receptors subsequent to antigen or lectin stimulation. These cytotoxic helper or suppressor T cells can now multiply freely only in the presence of TCGF.

Interleukin-2 that is practically free of phytohemagglutin (PHA) is a necessary component of any in-vitro multiplication (cloning) or in-vivo, animal-experimental or clinical, study or cultivation of these cytotoxic helper or suppressor T cells.

It is suspected that a large number of disruption in immune defense (immunological diseases) can be ascribed to the lack of interleukin-2 producers, to excessively low IL-2 production, or to the absence or insufficient formation of IL-2 receptors and can therefore be ameliorated by the administration of interleukin-2.

In diagnosing such conditions it is necessary to manufacture monoclonal antibodies to interleukin-2 to establish a diagnosis kit on a radioimmunoassay or enzyme-linked immunosorbent assay basis.

More recent research has also demonstrated that interleukin-2 formation decreases sharply with age. Foreign interleukin-2 could thus be employed to cure or ameliorate diseases caused by disruptions in its production in the body.

It has also been demonstrated that some tumor cells have surface antigens that can provoke immunostimulation of in-vitro T cells. It might be possible to utilize interleukin-2 to produce quantities of cytotoxic T cells. Mixing malignant cells with antologenous normal lymphocytes will lead to activation of the normal T cells. This in turn can be increased in culture with interleukin-2, and some of these T cells might be cytotoxic and could be used to kill tumor cells in vivo. Interleukin-2 is therefore also a potential anticancer agent.

Extremely pure interleukin-2, free not only of PHA but of other impurities as well, is, however, a prerequisite for all these purposes.

Methods of obtaining crude human interleukin-2 are described in
1. Ruscetti FW & Gallo RC, Regulation of the production and release of human T-cell growth factor, J. Supramol. Biol. 13 (1980),
2. Bonnard GD, Yakasa K, & Maca RD, Continued growth of functional human T lymphocytes: production of human T-cell growth factor, Cell Immunol. 51: 390–410 (1980),
3. Alvarex JM, Silva A, & de Landazuri MO, Human T-cell growth factor. I. Optimal conditions for its production, J. Immunol. 123: 977–83 (1979),
4. Ruscetti FW & Gallo RC, Human T lymphocyte growth factor: regulation of growth and function of T lymphocytes, Blood 57: 379 (1981), and
5. Lindsay P, Schwulera U, & Sonneborn HH, The species specificity of interleukin 2, 3rd International Lymphokine Congress, Dallas, Tex., Oct. 14–17, 1981.

The crude product, however, contains several substances that either inhibit or stimulate cell growth. Examples are phytohemagglutin (PHA), other mitogenic factors, interferon, and other factors that have not yet been more precisely characterized.

The mitogenic action of PHA, for example, disrupts many biological test systems because the effect of interleukin-2 being studied interferes with it, so that the cause of an effect can not be identified. Separating the PHA is a difficult biochemical problem because its molecule is not uniform but consists of 5 different molecules with molecular weights of from 33,000–128,000 amu (cf. Monsigny M, Roche AC, & Kieda C, Lectins as tools to study cell surface membranes, Pharmindustrie [L'Industrie Biologique Française], 1978).

The previous literature describes numerous purification processes, mainly however for the interleukin-2 obtained from various species of animals. Examples include
amonium-sulfate precipitation,
gel filtration,
DEAE-anion exchanger chromatography
CM- or SP-cation exchanger chromatography,
hydrophobic chromatography,
preparative polyacrylamide-gel electrophoresis, and
preparative isoelectric focussing
(cf.
6. Mier JW & Gallo RC, Purification and some characteristics of human T-cell growth factor from phytohemagglutinin-stimulated lymphocyte-conditioned media, Proc. Natl. Acad. Sci. 77: 6134 (1980)
and 4., above).

Such human interleukin-2 can not be isolated by single-stage purification. Several more or less effective stages, which often partially denature the protein, are necessary. This is at present connected with the properties of interleukin 2. The molecule of (human) interleukin-2 is small, with a molecular weight of 17,000 amu, and is negatively charged. It is readily hydrophobic and seems to adhere to the wall of a plastic-glass dialysis tube or to aggregate to itself. Losses are high in filtration sterilization, and even dialysis is possible only under certain conditions. Protein concentration is very low, it behaves like a hormone, and is highly active even at nanogram levels in the test system. The purer the product, the more unstable, so that the molecule must be stabilized at every stage of purification.

Of the methods mentioned in the foregoing, the first two are protein-preserving under certain conditions. Still, even when streamed together, they do not lead to a pure product.

All the other methods mentioned are highly protein-denaturing, with 50 to 95% of enzyme activity often getting lost at one single stage.

One of the purification methods described in the literature [6, p. 6137] is

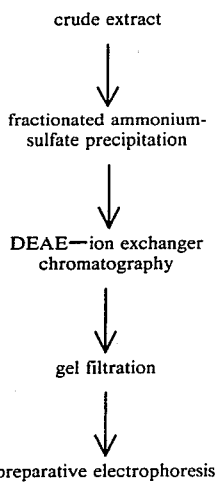

crude extract

↓ fractionated ammonium-sulfate precipitation

↓

DEAE—ion exchanger chromatography

↓ gel filtration

↓ preparative electrophoresis

A product purified in this way, however, is highly inactivated.

The invention is intended as a method of purifying human interleukin-2 that preserves the protein and yields a very pure, active, and stable product.

This objective is attained by subjecting crude interleukin-2 extract to group-selective dye-ligand absorption chromatography of one or more stages of purification with a matrix-gel medium consisting of a Blue A ligand or variant thereof or of a Green A ligand in a concentration of approximately 1.5 to 3.0 mg/ml of expanded matrix at a pH of approximately 6.8 to 8.5, a temperature of approximately 4° to 40° C., and a flowthrough rate of approximately 10 to 100 ml/h, employing an eluent.

The method in accordance with the invention yields an interleukin-2 product that is free of PHA and/or a very pure interleukin-2 product that can be used to make a diagnostic-test set, through monoclonal antibodies on a base of RIA or EIA, for example.

Of course, dye-ligand chromatography with Blue A and Green A has been utilized in the past to purify a number of enzymes and other proteins. Still, it has taken a lot of research in various potential methods of purification to find one that complies, in contrast to known methods, with the optimum prerequisites for the purification of human interleukin-2.

The advantage of the invention is the extremely low protein loss at each stage, resulting in an extremely high yield. Other methods, like DEAE chromatography or isoelectric focussing, are on the other hand very ineffective methods of purifying interleukin-2. Dye-ligand chromatography can also be employed as a first or second purification stage without the necessity of stabilizing the interleukin-2 because the human albumin that binds to the column will stabilize the factor simultaneously. If the column is utilized as a third purification stage, of course, stabilizing conditions will have to be applied.

The method in accordance with the invention can be carried as one stage at any point in a series of interleukin-2 purifications, following initial ammonium-sulfate precipitation and subsequent gel filtration for example. It can however also be employed as a sole or supplementary purification stage to separate the PHA. As mentioned in the foregoing, PHA is extremely difficult to separate. All the methods previously described separate only some. The method in accordance with the invention, however, removes 98 to 100% of the PHA, which is so disruptive to many immunological tests, in one sole stage.

When the method is employed as a supplementary purification stage, ammonium-sulfate precipitation for example can be employed as a further stage.

It is also of decisive importance for stabilization of the interleukin-2, which becomes very labile during purification, for human albumin to bind to the dye-ligand column simultaneously, as mentioned in the foregoing, which leads to stabilization during binding to the matrix and during elution. This is of decisive significance in the manufacture of an interleukin-2 preparation that is free of PHA.

Blue A has the formula

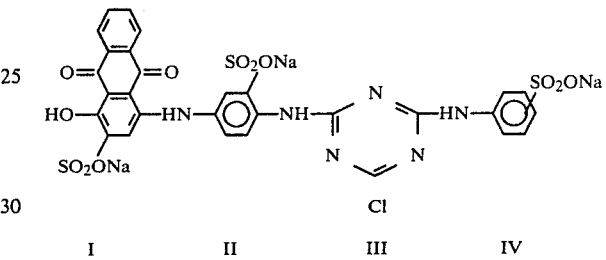

I  II  III  IV

It gets bound with an ether bond to the triazine ring of a matrix gel as follows:

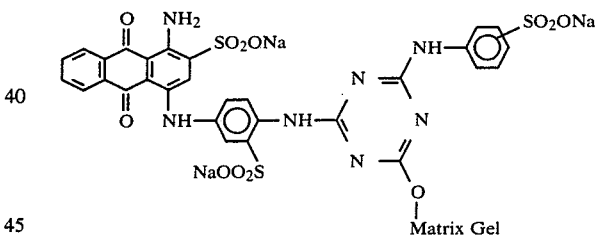

A thorough description of the Blue A ligand, its variations, the Green A ligand, and the matrix gels will be found in 7. Dye Ligand Chromatography, Amicon Corp., Publication 512 A (1980).

Agarose, preferably cross-linked, and sepharose, for example, are appropriate matrix gels.

The concentration of dye ligand ranges approximately from 1.5 to 3.0 and preferably 1.58 mg/ml of expanded matrix.

The strength with which the interleukin-2 binds to the ligand can be increased or decreased by varying the parameters pH,
ionic strength,
temperature,
sample volume,
column dimensions, and
flowthrough rate within the ranges being claimed or considered practical.

The pH can range from 6.8 to 8.5 (with the interleukin-2 forming a stronger bond with the matrix in a slightly acid environment).

Practically any appropriate salt can be employed as an eluent. Some examples are sodium chloride, potassium chloride, and other salts.

Ionic strength ranges from 0.01 to 2M.

Operating temperature ranges approximately from 4° to 40° C.

Sample volume can range approximately from 0.1 ml to several liters, depending on the dimensions of the column and on the amount of crude product available. The method can also be carried out in batches.

The column can range in size from 1 ml (0.5×2 cm) to 500 ml or more at a flowthrough rate of 10 to 100 ml/h.

The invention will now be specified with reference to the following examples.

EXAMPLE 1

Obtaining crude human interleukin-2

Whole human blood was sedimented for 1 hour at 1×g and 37° C. in the presence of oxypolygelatin citrate. Plasma and buffy coat were collected and centrifuged. The sediment was resuspended, layered on Ficoll-Hypane, and centrifuged 20 minutes at 1500×g 20 min. The mononuclear cells in the intermediate layer were washed twice in the medium by centrifuging at 250×g. Cells pooled from 3 donors received allogeneic and mitogenic (1% PHA-M) stimulations at a cell concentration of $10^6$/ml and were cultivated for 48 hours in RPMI-1640 to which had been added 25 mmoles of Hepes buffer, L-Gutamin, and antibiotics and 1% inactivated pooled human serum. The remainder, which contained the interleukin-2, was harvested by centrifuging, filtration sterilized, and stored at −20° C.

EXAMPLE 2

Single-stage purification

A Dyematrex ™ and Blue A ® column, manufactured by the Amicon Corp. (concentration of 1.58 ml of Blue A dye ligand/ml of expanded agarose) with a volume of 2 ml was regenerated with 5 times the column volume of 8M of urea in 0.5M of NaCl. It was then equilibrated with 10 times the volume of 20 mM of tris HCl at a pH of 7.5 and by subsequent washing with 10 times the volume of RPMI-1640 (a synthetic culturing medium with salts, buffers, amino acids, vitamins, and growth substances+L-glutamine, manufactured by Gibco). A 2-ml probe of interleukin-2 obtained by the method in Example 1 was processed at approximately 10 ml/h. 30 minutes after the sample had penetrated the column was washed with 5 times the column volume of 20 mM of tris HCl at a pH of 7.5. This was followed by elution with 10 ml of 1.5-M NaCl. All stages were conducted at 4° C.

The resulting product contained a high percentage of interleukin-2+albumin+γ-interferon, and no PHA could be detected in the eluate.

Figure 2:
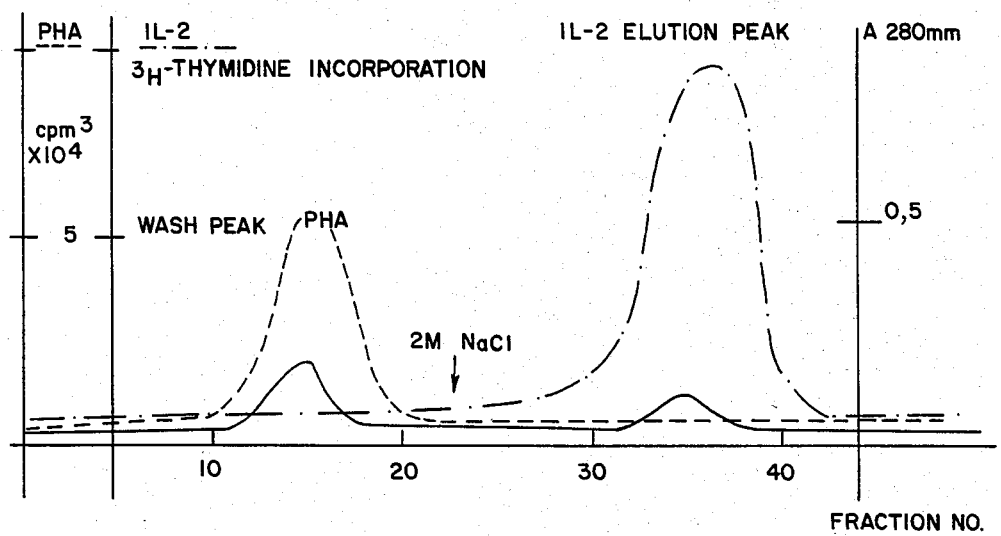

FIG. 2 illustrates the course of the chromatography described in the foregoing. Following chromatography the column was stored at 4° C. in the presence of 0.2% $NaN_3$.

EXAMPLE 3

Two-stage purification

1. Ammonium-sulfate precipitation
2. Blue A 6 g (55% saturation) of solid $(NH_4)_2SO_4$ was added slowly to 100 ml of the crude extract stirred at 4° C. Stirring was continued for 2 hours on a magnetic stirrer. The precipitate was then removed by 20 minutes of centrifuging at 4° C. and 50 000×g and removed. It contained primarily high-molecular proteins and PHA. Solid $(NH_4)_2SO_4$ was again added to attain a saturation of 90% and precipitated at 4° C. for 2 hours, the precipitate being centrifuged out for 20 minutes at 50 000×g in 10 ml of buffer composed of 0.01M of Na/K phosphate, pH 7.4 and
0.15M of NaCl.

The high concentration of $(NH_4)_2SO_4$ was removed by 2 to 3 hours of filtration dialysis with a PM10 membrane (amicon). Blue A chromatography was then conducted as described in Example 2. The table shows the results.

|  | ml | mg of protein | yield of IL-2* | PHA activity** |
|---|---|---|---|---|
| Crude extract | 100 | 25 | 100% | 100% |
| $(NH_4)_2SO_4$ | 10 | 19 | 90–95% | 30–40% |
| Blue A | 3 | 8 | 90% | 0% |

*The yield of interleukon-2 was calculated with an arbitrarily assumed IL-2 unit measured in accordance with a standard and the protein yield and hence a specific unit computed. Human MLC blasts or human PHA blasts were utilized as target cells and the $^3$H—thymidine incorporation measured after a 6h pulse. The long-term growth of cloned human T cells in the presence of IL-2 was also followed.
**PHA activity was determined with ν lymphoctyes as target cells as well as by $^3$H—thymidine incorporation.

Result

Interleukon-2 was concentrated through the Blue A segment and was somewhat impure, stabilized by simultaneously binding human albumin. PHA activity had been completely eliminated.

Overnight dialysis is just as successful as 2 to 3 hours of filtration dialysis.

EXAMPLE 4

Three-stage purification

1. Ammonium-sulfate precipitation (as in Ex. 3)
2. Gel filtration
3. Blue A (as in Ex. 2)

The first stage was conducted as in Example 3 although without filtration dialysis.

In the second stage, gel filtration, a column (2.5×100 cm) was charged with Sephadex G75 and equilibrated with a buffer consisting of 0.01M of Na/K phosphate, pH 7.4
0.15M of NaCl, and
0.01% of PEG 6000 (as a stablizer).

Figure 3:
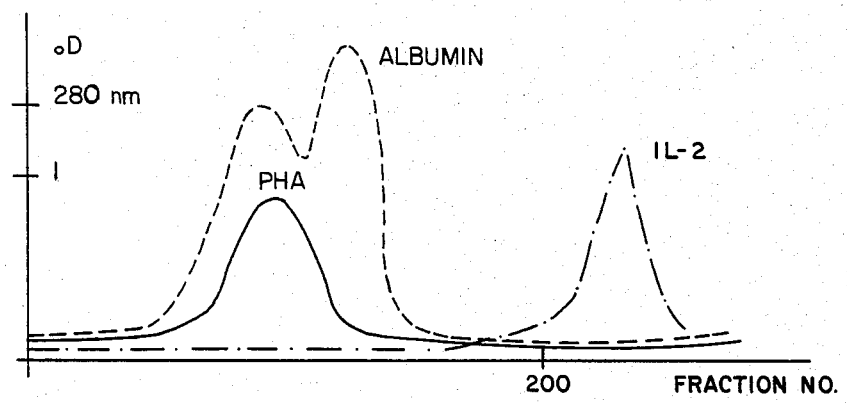

After calibrating the column with standard proteins, 10 ml of the solution obtained in the first stage were added to the column. Large serum proteins like albumin for example were simultaneously separated. FIG. 3 shows the elution curve.

Flowthrough rate was 25 m/h. Fraction size was 3 ml.

In the third stage, Blue A chromatography, 0.01% of the stabilizer PEG 6000 was, in deviation from Example 3, again added to the buffer.

Proteins with the same molecular weight as interleukin-2 but that do not bind to a Blue A column were separated during this stage.

EXAMPLE 5

Reference example to confirm inactivity

The methods in the table, some from the literature, were conducted with the raw extract to test their comparative applicability to the purification of human interleukin-2.

| Method | Loss of IL-2, % |
| --- | --- |
| Blue A | 5-10 |
| (NH$_4$)$_2$SO$_4$ | 5-10 |
| Gel filtration | 10-20 |
| Hydrophobic chromatography | 40-50 |
| Preparative gel electrophoresis (with and without detergent) | 50-60 |
| DEAE-anion exchange chromatography | 90-95 |
| CM-cation exchange chromatography | 90-95 |
| Preparative isoelectric focussing | 90-95 |
| Hydroxylapatite chromatography | 80-90 |

Text 6 of the bibliography was reworked with the following results:

| | Yield of IL-2, % |
| --- | --- |
| Crude extract | 100 |
| (NH$_4$)$_2$SO$_4$ | 90-95 |
| DEAE | 1-5 |
| Gel filtration | <0.1 |
| Gel electrophoresis | <0.01 |

I claim:

1. A method of purifying human interleukin-2 comprising passing crude interleukin-2 extract through a group-selective dye-ligand adsorption chromatographic column containing a matrix-gel medium consisting of a Blue A ligand or variant thereof or of a Green A ligand in a concentration of approximately 1.5 to 3.0 mg/ml of expanded matrix at a pH of approximately 6.8 to 8.5, a temperature of approximately 4° to 40° C., and a flow-through rate of approximately 10 to 100 ml/h, and eluting purified interleukin-2 from the medium.

2. A method according to claim 1, wherein the ligand is Blue A ligand.

3. A method according to claim 1, wherein the matrix gel medium comprises 5% agarose.

4. A method according to claim 1, wherein elution is effected with NaCl or KCl.

5. A method according to claim 1, wherein prior to passage through the column the crude interleukin-2 is contacted with solutions of different concentrations of ammonium sulfate to effect selective precipitation in stages and the desired fractions are filtered to remove gels.

6. A method according to claim 1, wherein the process is repeated at least once more on the eluted product.

* * * * *

UNITED STATES PATENT AND TRADEMARK OFFICE
CERTIFICATE OF CORRECTION

PATENT NO. : 4,508,833
DATED : April 2, 1985
INVENTOR(S) : Hans H. Sonneborn, et al It is certified that error appears in the above-identified patent and that said Letters Patent is hereby corrected as shown below:

1st Page, under "U.S. Patent Documents"  Line 2 delete "Fabricus" and substitute --Fabricius--

Col. 4, line 26  Delete bottom of formula I and substitute:

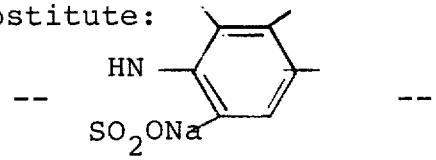

Col. 4, line 40  Delete middle of formula and substitute:

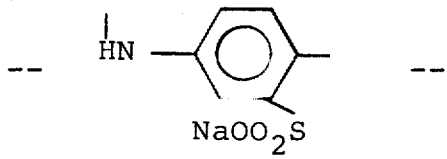

Col. 5, line 43  After "Blue A" delete "®" and substitute -- © --

Signed and Sealed this

Fifteenth Day of October 1985

[SEAL]

Attest:

DONALD J. QUIGG

Attesting Officer

Commissioner of Patents and Trademarks—Designate